United States Patent

Mabon et al.

Patent Number: 5,890,500
Date of Patent: Apr. 6, 1999

[54] ORTHODONTIC BRACES WEARER DENTAL FLOSSING DEVICE

[76] Inventors: Robert Alan Mabon; Crystal Elayne Mabon, both of 503 Joyce St., Apollo, Pa. 15613

[21] Appl. No.: 876,360
[22] Filed: Jun. 14, 1997
[51] Int. Cl.⁶ ..................................... A61C 15/00
[52] U.S. Cl. ........................................ 132/323; 132/321
[58] Field of Search .................... 132/321, 323, 132/324

[56] References Cited

U.S. PATENT DOCUMENTS

| | | | |
|---|---|---|---|
| 4,011,658 | 3/1977 | Tarrson et al. | 132/329 |
| 5,050,625 | 9/1991 | Siekmann | 132/329 |
| 5,392,794 | 2/1995 | Striebel | 132/321 |
| 5,735,299 | 4/1998 | Kaltenbach | 132/321 |

Primary Examiner—John J. Wilson

[57] ABSTRACT

This invention describes a device and process used to aid in flossing the teeth of an Orthodontic Appliances (braces) patient. The device is a short, thin "spaghetti" sized guide tube combined with dental floss. A length of floss is inserted into the guide tube. The floss and guide tube are easily pushed into the space between the user's teeth and the braces inserting the floss. The guide tube is removed from the space and allowed to rest on an unemployed section of floss. The guide tube is slightly coiled during manufacture and clings to the unemployed section of floss and does not require rethreading of the floss through the guide tube for each tooth. The procedure is repeated for subsequent teeth. A modified tube version includes an enlarged funnel like end to simplify the threading of floss into the tube.

15 Claims, 2 Drawing Sheets

NOTE: NOT TO SCALE

NOTE:
NOT TO SCALE

NOTE:
NOT TO SCALE

NOTE:
NOT TO SCALE

ORTHODONTIC BRACES WEARER DENTAL FLOSSING DEVICE

FIELD OF THE INVENTION

This invention generally relates to devices and processes used to aid in flossing teeth. More specifically, it is an aid to positioning floss into the area between Orthodontic Appliances such as braces and the wearer's teeth.

BACKGROUND OF THE INVENTION

It is generally accepted that regular flossing reduces the frequency of dental caries, peritonitis, gingivitis and ultimately premature tooth loss. Flossing is an effective method of removing stubborn food particles and plaque from between teeth and gums. A typical floss session requires a few minutes to complete for an experienced user without Orthodontic Appliances such as and hereafter known as braces. Braces, by inspection add to the complexity of and time to floss. Dental floss is relatively limp much like a seamstress's thread as this allows the floss to conform to most dental shapes. However, floss's relative limpness also makes it difficult to thread through restricted areas such as the space between braces and teeth.

With the introduction of Orthodontics to dentistry, millions of patients young and old with maligned teeth and or bite imperfections have received corrective Orthodontics. Each year approximately 1.6 million new Orthodontic procedures are performed at a rate increasing by more than 50% from the years 1982 through 1994 as per surveys conducted by the American Association of Orthodontics. Corrective Orthodontic procedures include proper alignment of teeth misplaced due to premature loss of primary teeth, up to preparing adequate room for exposed or unexposed secondary teeth or dental bridges. Bite imperfections such as over, under or laterally maligned jaw structures can be corrected. The medical and cosmetic value of these procedures can be inferred from the increasing number of patients.

Braces are comprised of metallic, plastic or ceramic plates known as brackets bonded to the teeth with an adhesive. The brackets are interconnected with various wires, springs and chains hereafter known as wires. The wires connected to the brackets physically reposition the teeth and possibly bone structure during the treatment period. Such orthodontic procedures can last from several weeks to many years and cost thousands of dollars. Ultimately, a requisite for successful treatment includes thorough brushing and flossing during the treatment period. By inspection, braces impede brushing and flossing and dictate specialized devices to adequately clean teeth. In flossing, the interconnecting wires inhibit positioning floss between teeth and down to the gum line. The area created between the teeth and brace wire is hereafter known as the dental area.

One device designed to aid flossing is U.S. Pat. No. 4,011,658 (Butler EEZ-THRU). This device consists of a thin loop of synthetic thread-like material that generally works in a manner similar to a sewing needle threading device. Limitations to this system are the floss generally must be re-threaded through the loop for each tooth to be flossed and can be slower to use than the proposed guide tube.

Three U.S. Pat. Nos. 4,008,727 (Oral B Super Floss), 5,050,625 Dental Floss Threading Device and 5,392,794 Dental Floss for Brace Wearers And The Like, generally require to user to use only their respective brand of floss and not the user's prefered brand.

Ultimately, one device would include the features:
1. Retain floss within device during floss session, eliminating need to re-thread floss for each tooth.
2. Allow user to select brand and/or type of floss.
3. Allow simple threading of floss into device.
4. Allow simple threading of floss and device into the dental area.

SUMMARY

The purpose of this invention is a device and process to aid flossing the teeth of an orthodontic brace patient. This device is a length of "spaghetti" sized guide tubing combined with the application of conventional dental floss. The user cuts off a sufficient length of dental floss and inserts it through the tube. The floss and tube are quickly and easily inserted into the dental area between the teeth and brace wire. The guide tube may be passed completely through or withdrawn from this area while a section of floss is held by the user and allowed to remain in the dental area. The guide tube is allowed to rest on an unemployed section of the floss. Conventional flossing proceeds. As the tube is coiled about its length during manufacturing and has a "memory" of this coiling, the tube clings to and remains on the unemployed section of floss. The system is automatically ready to use on subsequent teeth, thus shortening overall floss time. This system requires the user to thread the floss through the guide tube only once per floss session, is reusable, economical and simple to use. A modified version of the guide tube includes and enlarged funnel like end to simplify threading floss into the tube.

DESCRIPTION OF THE PREFERRED EMBODYMENT(S)

Figure 1:
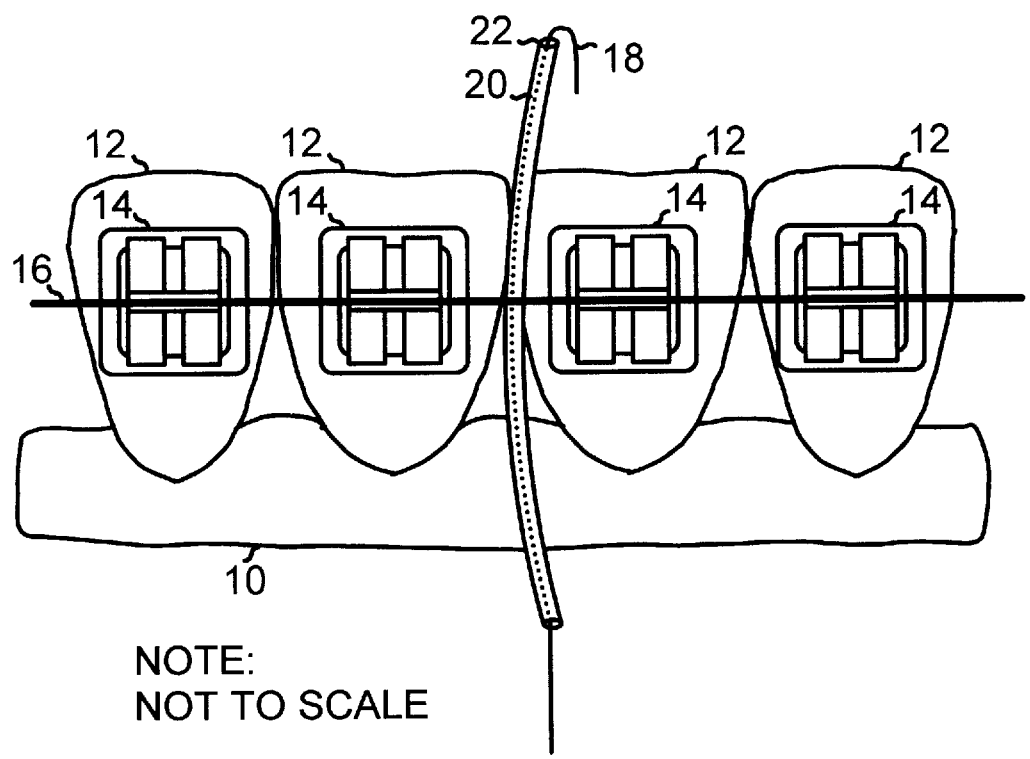
FIG. 1 is a perspective view of the "spaghetti" guide tube and floss assembley inserted into the space created by the brace wire and teeth.

FIG. 1 depicts the invention in use. The guide tube 20 is comprised of a suitable length of flexible, hollow material such as but not limited to tubing comprised of TFE. The tubing is sold commercially by several manufactures. Other combinations of synthetic material such as PVC or natural materials like rubber could be fabricated to produce similar functional characteristics. The guide tube 20 is cut to a length that is easy to grasp by the user's fingers and includes a suitable length remaining to be inserted through the dental area. The guide tube 20 is generally 1½ inches in length and could vary from 1 to 3 inches in length if desired. The hollow interior of the guide tube 20 is of sufficient dimension to allow insertion of the floss 18. The external dimension of the guide tube 20 is limited to roughly the clearance dimension between brace wire 16 and teeth 12.

The teeth 12 generally are supported naturally by gum tissue 1. The orthodontic brace brackets 14 have been previously bonded to the teeth 12 in an corrective orthodontic procedure. The brace wire 16 has been previously attached to the brackets 14. It is the brace wire 16 that impedes inserting the floss.

The invention is utilized by threading a length of floss 18 through the guide tube 20, such that the floss 18 protrudes from each end of the guide tube 20. A sufficient length of floss 18, typically a few inches, is extended past the guide tube work end 22 as this allows the user to grasp the floss 18 when the guide tube work end 22 has been positioned through and past the brace wire 16 and teeth 12. The floss 18 and guide tube 20 are then inserted into the area between the user's teeth 12 and brace wire 16. The guide tube 20 is withdrawn completely from or pushed completely through the area and allowed to rest on an unemployed section of floss 18 at a sufficient distance from the tooth 12 to allow flossing. The slight natural coiling action about the length of the guide tube 20 inhibits the guide tube 20 from slipping off the floss. The user then flosses as usual.

After a tooth 12 is flossed, the floss 18 is withdrawn from the area. The guide tube 20 is then repositioned on the floss 18 to allow a repeat of the insertion process. When the floss session is complete, the guide tube 20 may be rinsed and stored for future use or discarded, as the guide tube 20 is economical enough to be replaced each floss session.

Figure 2:
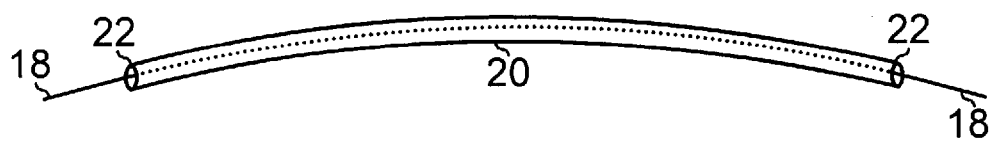
FIG. 2 is a perspective view of a guide tube section suitable for use as described herein.

FIG. 2 depicts the guide tube 20 in its natural form. As the guide tube 20 shown in FIG. 1 and FIG. 2 is unidirectional, the guide tube work end 22 is that which first passes between teeth 12 and wire 16. Through manufacturing, the tube 20 exhibits a slight coiling action about it's length in form of varying magnitude. The characteristic of the guide tube 20 clinging to the floss 18 while the user flosses is dependent on this coiling feature and the resulting frictional forces. This device is the most economical to produce as it is commercially available and merely cut to length. The guide tube 20 exhibits enough rigidity to thread through the dental area, yet is pliable enough to minimize gum 10 injury should contact between guide tube 20 and gum 10 occur.

Figure 3:
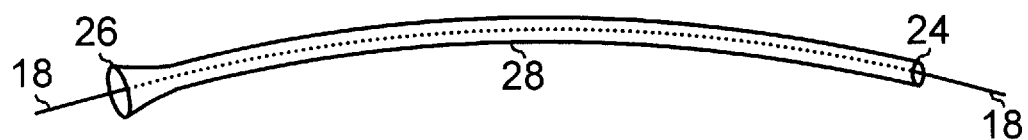
FIG. 3 is a perspective view of a guide tube section modified with a funnel like end to ease insertion of floss, also described herein.

FIG. 3 depicts an enhanced version of the guide tube 28. The work end 24 is similar to the work end 22 of FIG. 2. The thread end 26 is enlarged to facilitate insertion of the floss 18. The guide tube 28 reduces the accuracy and manual dexterity required of the user, benefiting those with coordination difficulties. The thread end 26 is pliable enough to be collapsed about the guide tube's 28 length and return to near its original form. Hence, the guide tube 28 is employed in a manner similar to the guide tube 20 of FIG. 1 and FIG. 2 as described above.

Through manufacturing, the tube 28 also exhibits a slight coiling action about it's length in form of varying magnitude. This guide tube 28 also clings to the floss 18 while the user flosses because of this coiling feature and the resulting frictional forces.

We claim:

1. A guide tube for inserting dental floss between teeth and orthodontic appliances, comprising a resilient flexible hollow tube, said tube approximately 1 to 3 inches in length, said tube of sufficient internal dimension to allow insertion of dental floss through the tube, and of limited outside dimension to allow partial or complete passage of said tube between teeth and said appliances, the improvements which comprise:

(a) said guide tube constructed essentially of TFE (Tetraflouroethylene) PTFE (Polytetrafluoroethylene), PVC (Polyvinylchloride), FEP (Fluorinated ethylene-propylene), PFA (Perfluoroalkoxy), or PE (Polyethylene);

(b) said guide tube curved about its entire length;

(c) said guide tube having a single length of floss inserted through and contained within said guide tube body, and said floss protruding from each said guide tube end;

(d) said guide tube being manually slideable along the length of said floss;

(e) said guide tube remaining on the length of said floss during use.

2. Guide tube according to claim 1 wherein said TFE, PTFE, PVC, FEP, PFA or PE construction allows insertion of relatively limp dental floss through tube.

3. Guide tube according to claim 1 wherein said guide tube has a round, elliptical or any polygonal cross sectional area.

4. Guide tube according to claim 1 wherein said guide tube is sufficiently curved about its entire length to inhibit said guide tube from sliding off of said floss during flossing due to friction.

5. Guide tube according to claim 1 wherein said guide tube being manually slideable along the length of said floss allowing the user to rest said guide tube on an unemployed section of said floss.

6. Guide tube according to claim 1 wherein said guide tube remains on the length of said floss during use allowing the user to insert said floss into and through the tube body only once per floss session.

7. A method according to claim 1 for flossing teeth of orthodontic appliance wearers comprising the steps of:

(a) preparing a suitable length of said guide tube, sufficiently curved about its length, generally one (1) to three(3) inches in length said guide tube device of suitable internal dimension ranging 0.025 to 0.045 inches and suitable outside dimension ranging 0.032 to 0.072 inches;

(b) preparing a suitable length of user preferred dental floss sufficient for one (1) floss session, generally but not limited to twelve(12) to twenty-four(24) inches;

(c) inserting said floss into and through said guide tube body such that said floss protrudes from each end of said guide tube;

(d) positioning said guide tube and said floss combination sufficiently through dental area comprising teeth and orthodontic appliances to permit grasping of said floss on opposite side of said floss and said guide tube entry point and subsequent removal of said guide tube from said dental area in the same or opposite direction of said insertion;

(e) slideably positioning said guide tube at an unemployed location on said floss and allowing said guide tube to remain on said floss while said floss is employed;

(f) removing said floss from said dental area and repeating steps (d) and (e) until floss session is finished;

(g) discard said floss, rinse and store said guide tube for subsequent use or discard said guide tube when worn.

8. A guide tube for inserting dental floss between teeth and orthodontic appliances, comprising a resilient flexible hollow tube curved about its entire length, modified using a heating and die forming process, said tube approximately 1 to 3 inches in length, said tube of sufficient internal dimension to allow insertion of dental floss through the tube, and of limited outside dimension to allow partial or complete passage of said tube between teeth and said appliances, the improvements which comprise:

(a) said guide tube constructed essentially of TFE (Tetrafluoroethylene) PTFE (Polytetrafluoroethylene), PVC (Polyvinylchloride), FEP (Fluorinated ethylene-propylene), PFA (Perfluoroalkoxy), or PE (Polyethylene);

(b) said guide tube curved about its entire length;

(c) said guide tube including one end enlarged in a funnel-like form;

(d) said guide tube having a single length of floss inserted through and contained within said guide tube body, and said floss protruding from each said guide tube end;

(e) said guide tube being manually slideable along the length of said floss;

(f) said guide tube remaining on the length of said floss during use.

9. Guide tube according to claim 8 where said TFE, PTFE, PVC, FEP, PFA, PE construction allows insertion of relatively limp dental floss through tube.

10. Guide tube according to claim 8 wherein said guide tube has a round, elliptical or any polygonal cross sectional area.

11. Guide tube according to claim 8 wherein said guide tube is sufficiently curved about its entire length to inhibit said guide tube from sliding off of said floss during flossing due to friction.

12. Guide tube according to claim 8 wherein said enlarged funnel like end simplifies insertion of said floss into said guide tube.

13. Guide tube according to claim 8 wherein said guide tube being manually slideable along the length of said floss allowing the user to rest said guide tube on an unemployed section of said floss.

14. Guide tube according to claim 8 wherein said guide tube remains on the length of said floss during use allowing the user to insert said floss into and through the tube body only once per floss session.

15. A method for flossing teeth of orthodontic appliance wearer comprising using the guide tube of claim 8 and the steps of:

(a) preparing a suitable length of said guide tube, sufficiently curved about its length, generally one (1) to three(3) inches in length said guide tube device of suitable internal dimension ranging 0.025 to 0.045 inches and suitable outside dimension ranging 0.032 to 0.072 inches;

(b) preparing a suitable length of user preferred dental floss sufficient for one (1) floss session, generally but not limited to twelve(12) to twenty-four(24) inches;

(c) inserting said floss into and through said guide tube body such that said floss protrudes from each end of said guide tube;

(d) positioning said guide tube and said floss combination sufficiently through dental area comprising teeth and orthodontic appliances to permit grasping of said floss on opposite side of said floss and said guide tube entry point and subsequent removal of said guide tube from said dental area in the same or opposite direction of said insertion, said enlarged funnel like end flexing sufficiently to pass through said dental area;

(e) slideably positioning said guide tube at an unemployed location on said floss and allowing said guide tube to remain on said floss while said floss is employed;

(f) removing said floss from said dental area and repeating steps (d) and (e) until floss session is finished;

(g) discard said floss, rinse and store said guide tube for subsequent use or discard said guide tube when worn.

* * * * *